United States Patent
Feith et al.

(10) Patent No.: US 10,837,565 B2
(45) Date of Patent: Nov. 17, 2020

(54) CHECK VALVE WITH INTEGRATED FILTER

(71) Applicant: CareFusion 303, Inc., San Diego, CA (US)

(72) Inventors: Raymond P. Feith, Chino Hills, CA (US); Eugene Mason, La Habra Heights, CA (US)

(73) Assignee: CareFusion 303, Inc., San Diego, CA (US)

( * ) Notice: Subject to any disclaimer, the term of this patent is extended or adjusted under 35 U.S.C. 154(b) by 8 days.

(21) Appl. No.: 16/205,122

(22) Filed: Nov. 29, 2018

(65) Prior Publication Data
US 2020/0173567 A1    Jun. 4, 2020

(51) Int. Cl.
*F16K 15/14* (2006.01)

(52) U.S. Cl.
CPC ......... *F16K 15/14* (2013.01); *Y10T 137/7888* (2015.04)

(58) Field of Classification Search
CPC .............. Y10T 137/7888; F16K 15/14; A61M 2005/1652
USPC ........................................................ 137/843
See application file for complete search history.

(56) References Cited

U.S. PATENT DOCUMENTS

| 3,889,710 A | 6/1975 | Brost |
| 6,105,609 A * | 8/2000 | Polidan ................. F16K 15/141 |
| | | 137/515.7 |

FOREIGN PATENT DOCUMENTS

| KR | 101888473 B1 | 8/2018 |
| WO | WO-2010107597 A1 | 9/2010 |
| WO | WO-2014107436 A1 | 7/2014 |
| WO | WO-2017062110 A1 | 4/2017 |

OTHER PUBLICATIONS

International Search Report and Written Opinion for Application No. PCT/US2019/059238, dated Jan. 24, 2020, 15 pages.

* cited by examiner

*Primary Examiner* — P. Macade Nichols
(74) *Attorney, Agent, or Firm* — Morgan, Lewis & Bockius LLP

(57) ABSTRACT

A check valve may include an upper housing defining an inlet, a lower housing defining an outlet, and a cavity interposed between and defined by the upper and lower housings for fluidly connecting the inlet and the outlet. The check valve may further include a flexible valve member mounted in the cavity to selectively permit fluid flow in a first direction, and prevent fluid backflow in a second direction opposite to the first direction. A filter member may be mounted in the upper housing, upstream of the flexible valve member. The filter member may have an elongated portion configured to maximize surface area thereof exposed to the fluid flow, and restrict passage of undesirable matter in fluid flowing through the check valve.

18 Claims, 3 Drawing Sheets

CHECK VALVE WITH INTEGRATED FILTER

TECHNICAL FIELD

The present disclosure generally relates to check valves, and more particularly to check valves having filtering mechanisms for filtering particulate matter in fluid flowing through the check valve.

BACKGROUND

Patients are commonly injected with IV solutions that are initially provided in an IV reservoir (a bottle or bag) and dripped into the vein of the patient through an IV line. Typically, an injection port is provided along the IV line and adapted to function with a syringe to permit an injectate to be added to the IV solution. A check valve is also commonly included in the IV line to permit fluid flow only in the direction of the patient. This ensures that the injectate flows downstream toward the patient, not upstream toward the IV reservoir.

SUMMARY

IV check valves are normally closed when there is no movement of fluid (e.g., infusion solution) through the IV set. For example, when there is no movement of fluid, the check valve is closed and does not allow fluid to pass the inlet port. When the fluid flows through the IV set, IV check valves open and allow the fluid to flow from one end of the IV check valve to the other end. However, many valves are susceptible to lodging grit and particulates. When reverse flow is applied while the grit is lodged, the inlet port does not fully seal and creates a small leak which renders the valve to be useless.

Providing an IV check valve with an integrated filter member that prevents grit lodging that leads to leaks and backflows of the fluid would be advantageous. Described herein are check valves having integrated filters that achieve these desired functions and objectives.

A check valve includes an upper housing defining an inlet of the check valve, a lower housing defining an outlet of the check valve; and a cavity interposed between and defined by the upper and lower housings for fluidly connecting the inlet and the outlet. The check valve further includes a flexible valve member mounted in the cavity to selectively permit fluid flow in a first direction, and prevent fluid backflow in a second direction opposite to the first direction, and a filter member mounted in the upper housing upstream of the flexible valve member. The filter member has an elongated portion configured to maximize surface area thereof exposed to the fluid flow and restrict passage of undesirable matter in fluid flowing through the check valve.

A check valve includes an upper housing including an inlet of the check valve, a lower housing axially coupled to the upper housing and comprising an outlet of the check valve, and a cavity cooperatively formed by the upper and lower housings for fluidly connecting the inlet and the outlet. The check valve further includes a flow passage extending between the inlet and outlet and fluidly communicated with the cavity, a flexible valve member mounted in the cavity, and an elongate filter member mounted in the flow passage upstream of the flexible valve member. The flexible valve member selectively permits fluid flow in a first direction, and prevents fluid backflow in a second direction opposite to the first direction. The elongate filter member maximizes surface area thereof exposed to the fluid flow, and restricts passage of undesirable matter in fluid flowing towards the flexible valve member.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

The present description relates in general to check valves, and more particularly, for example and without limitation, to check valves having filtering mechanisms for filtering particulate matter in fluid flowing through the check valve. The present check valves described herein provide a filter mechanism having a cylindrical elongated portion which provides an extended and increased filtering surface area through which the fluid flows as compared with conventional filters. The increased surface area advantageously allows for improved and enhanced filtering capabilities of the fluid as it flows from the inlet to the outlet of the check valve. Additionally, since the filter mechanism is elongated in shape, a diameter of the filter mechanism, and thus a corresponding size of the check valve in which it is housed, may be minimized.

In accordance with various embodiments, the filter mechanism may be formed of a porous material be capable of withstanding backpressures resulting from reverse flow of up to 200 KPa. Advantageously, the latter configuration may minimize the possibility of the filter mechanism collapsing under the backpressure resulting from reverse fluid flow. Furthermore, the check valve may include at least one axially extending stop that functions to prevent the filter mechanism from being displaced upwards into the inlet when excessive back pressures are experienced in the check valve. Due to the presence of the stop, the filter mechanism is prevented from being displaced upwards and into the valve inlet as a result of the force exerted by the deflected valve member. As such, the filter mechanism advantageously may act as a support or safeguard to protect the valve member from excessively bowing out when excessive reverse flow pressure is experienced.

Figure 1:
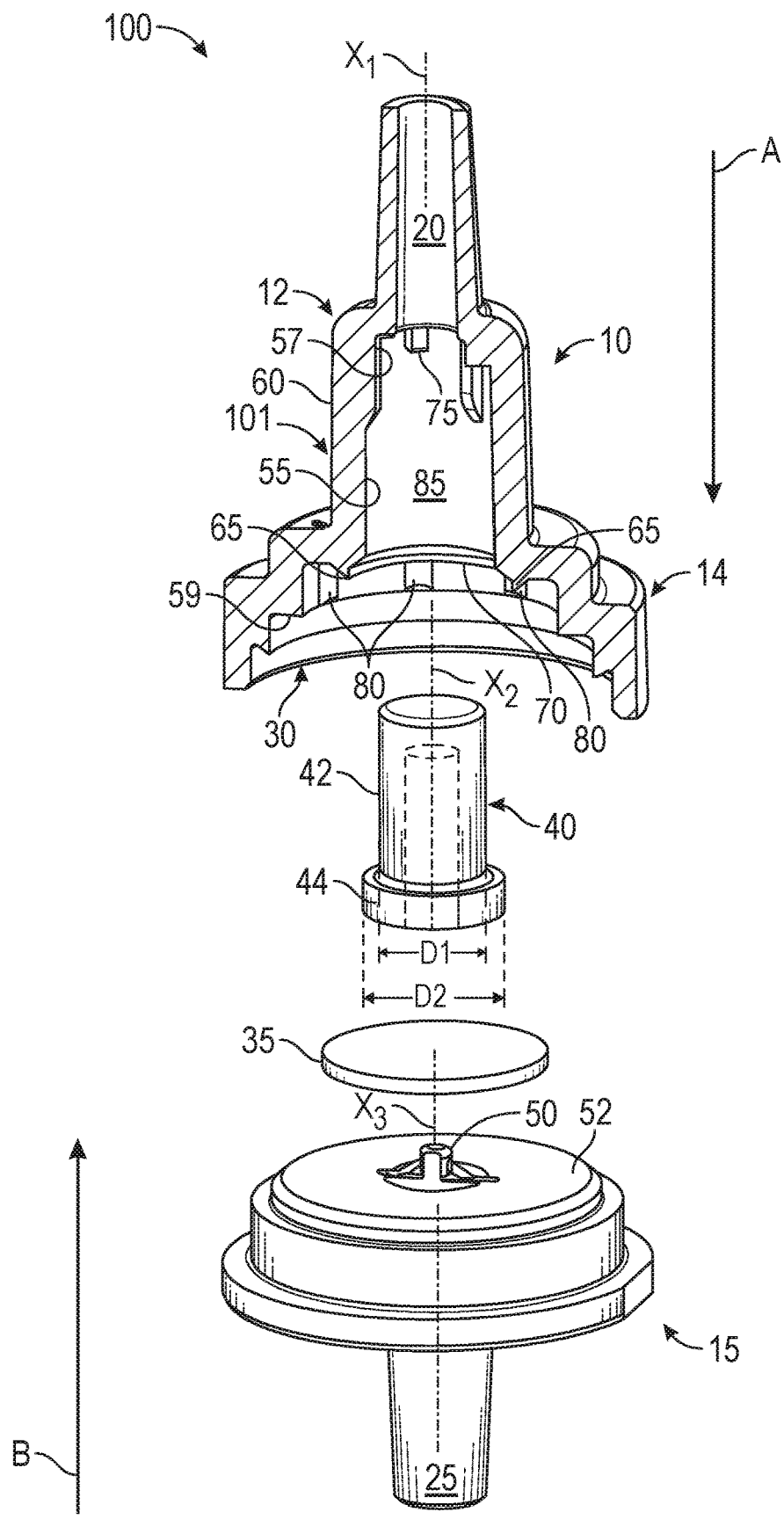
FIG. 1 is an exploded view of a check valve, in accordance with some embodiments of the present disclosure.

FIG. 1 is an exploded view of a check valve 100, in accordance with some embodiments of the present disclosure. As depicted, a top portion of the check valve 100 (i.e., an upper housing 10) is displayed in cross-sectional view to more clearly illustrate some of the features of the check valve 100. Referring to FIG. 1, the check valve 100 includes an axially extending body 101 defining a central longitudinal axis $X_1$. The body 101 may be a generally cylindrical (or tubular) structure and may include an upper housing 10 and a lower housing 15. The upper housing 10 may include a first end portion 12 and an axially opposite second end portion 14. As illustrated, a radial extent of the upper housing 10 at the second end portion 14 may be greater than the radial extent thereof at the first end portion 12. The lower housing 15 may include an upstream internal surface 52, and the second end portion 14 and the upstream internal surface 52 of the lower housing 15 may axially contact each other to co-operatively form a cavity 30 of the check valve 100.

The upper housing 10 may include an inlet 20 of the check valve 100 at the first end 12, and the lower housing 15 may include an outlet 25 of the check valve 100. The body 101 may define an internal flow passage 85 axially extending between the inlet 20 and the outlet 25 and in fluid communication therewith. As is understood, the check valve 100 may permit fluid to flow from the inlet 20 to the outlet 25 (as indicated by arrow A), and minimize, or otherwise limit, fluid flow from the outlet 25 to the inlet 20 (as indicated by arrow B). As depicted, the upper housing 10 and the lower housing 15 may define the cavity 30 for fluidly connecting the inlet 20 and the outlet 25. In the depicted embodiments a flexible valve member 35 may be mounted in the cavity 30 to selectively permit fluid flow in a first direction (indicated by arrow A), and prevent fluid backflow (reverse flow) in a second direction opposite to the first direction (indicated by arrow B). The valve member 35 may be mounted on a support portion 50 of the lower housing 14. As illustrated in FIG. 1, the support portion 50 may be centrally disposed in the cavity 30, and a central axis $X_3$ of the support portion may be coaxially aligned with the central longitudinal axis $X_1$ of the body 101. The support portion 50 may be coupled to, integrally formed with, or otherwise protrude from the upstream internal surface 52 of the lower housing 15, and extend into the cavity 30. As discussed in further detail below, the cavity 30 may form a part of the internal flow passage 85, or may be otherwise fluidly communicated with the internal flow passage 85 and therefore, fluid flowing from the inlet 20 to the outlet 25 may flow via the cavity 30.

In accordance with some embodiments, a filter member 40 defining a central longitudinal axis $X_2$ may be mounted in the upper housing 10 at a position upstream of the flexible valve member 35. The filter member 40 may have an elongate shape configured to maximize surface area of the filter member 40 that is exposed to the fluid flow. In this manner, the filter member may be configured to restrict and minimize passage of undesirable matter in the fluid flowing through the check valve 100. For example, as depicted, the filter member 40 may be formed in the shape of an inverted "T" or the shape of a top hat. To this effect, the filter member 40 may include an elongated stem portion 42 and a head portion 44. The aforementioned configuration is advantageous in that the elongated stem portion provides an extended and increased filtering surface area through which the fluid flows as compared with conventional filters. The increased surface area allows for improved and enhanced filtering capabilities of the fluid as it flows from the inlet 20 to the outlet 25.

In the depicted embodiments, the filter member 40 may be mounted in a cavity defined by the internal flow passage 85 in the upper housing 10. As depicted, and as shall be described in further detail below with respect to FIG. 2, the filter member 40 may be press-fit into the upper housing at a position upstream of the valve member 35. Press-fitting the filter member 40 in the upper housing eliminates the need for using traditional fastening and bonding techniques, which may require additional equipment and materials, and thereby increase complexity of the assembly and associated costs. Thus, the aforementioned configuration provides a simple, cost-effective, and mechanically robust filter-integrated check valve assembly.

In other embodiments, the filter member 40 may be coupled or bonded to internal walls of the upper housing 10 within the cavity defining the interior flow passage 85. For example, the filter member 40 may be bonded through any appropriate methods including, but not limited to ultrasonic welding, heat sealing, insert molding, gluing or other attachment methods. In some embodiments, at least the head portion 44 of the filter member 40 may be integrally formed with internal walls of the upper housing 10 as part of the molding process of the upper housing 10.

According to various embodiments of the present disclosure, at least a portion of the filter member 40 may devoid of material. For example, the filter member 40 may include a hollow central channel 72 which extends longitudinally through the central axis $X_2$ of the filter member 40. As depicted, the hollow central channel 72 may extend partially though the stem portion 42, and all the way through the head portion 44. In other embodiments, however, the hollow central channel 72 may extend only partially through each of the stem portion 42 and the head portion 44. In operation, fluid flows from the inlet 20, into the internal flow passage 85, where it is filtered by the filter member 40. As depicted in greater detail in FIG. 3, the fluid flows from the internal flow passage 85 into the filter member 40 through the top surface 58 and sidewall 68 of the stem portion 42, and through the head portion 74 of the filter member 40. In some embodiments, the fluid filtered in the stem portion 42 of the filter member 40 then travels into the central channel 72, past the valve member 35 (when in the open state) and into the outlet 25 to exit the check valve 100.

The filter member 40 may be formed of a porous material capable of preventing particulate matter of a particular size from passing through and potentially reaching and causing failure of the valve member 35. For example, the filter member 40 may be formed of a porous plastic material. Alternatively, the filter member 40 may be made of a non-woven cast material, a cork material, or any other porous fabric or material. The filter member 40 may be formed with a plurality of small holes or it may be woven, to provide pores of about 0.2 to 100.0 microns in size. In some embodiments, filter member 40 may be a flexible material such as a metal or polymeric material which is capable of maintaining the "inverse T" or "top hat" shape under fluid pressure. Further, filter member 40 may be made of a non-swelling material so as to maintain a gap between the stem portion 42 and an internal wall or surface of the upper housing 10, as shall be discussed in further detail below. In some embodiments, the filter member 40 may be formed of a material capable of withstanding or filtering flow rates of between 3 to 8 liters per hour. Additionally, the filter member 40 may be formed of a porous material capable of withstanding backpressures resulting from reverse flow of up to 200 KPa. Advantageously, the latter configuration may minimize the possibility of the filter member 40 collapsing under the backpressure resulting from reverse fluid flow.

Figure 2:
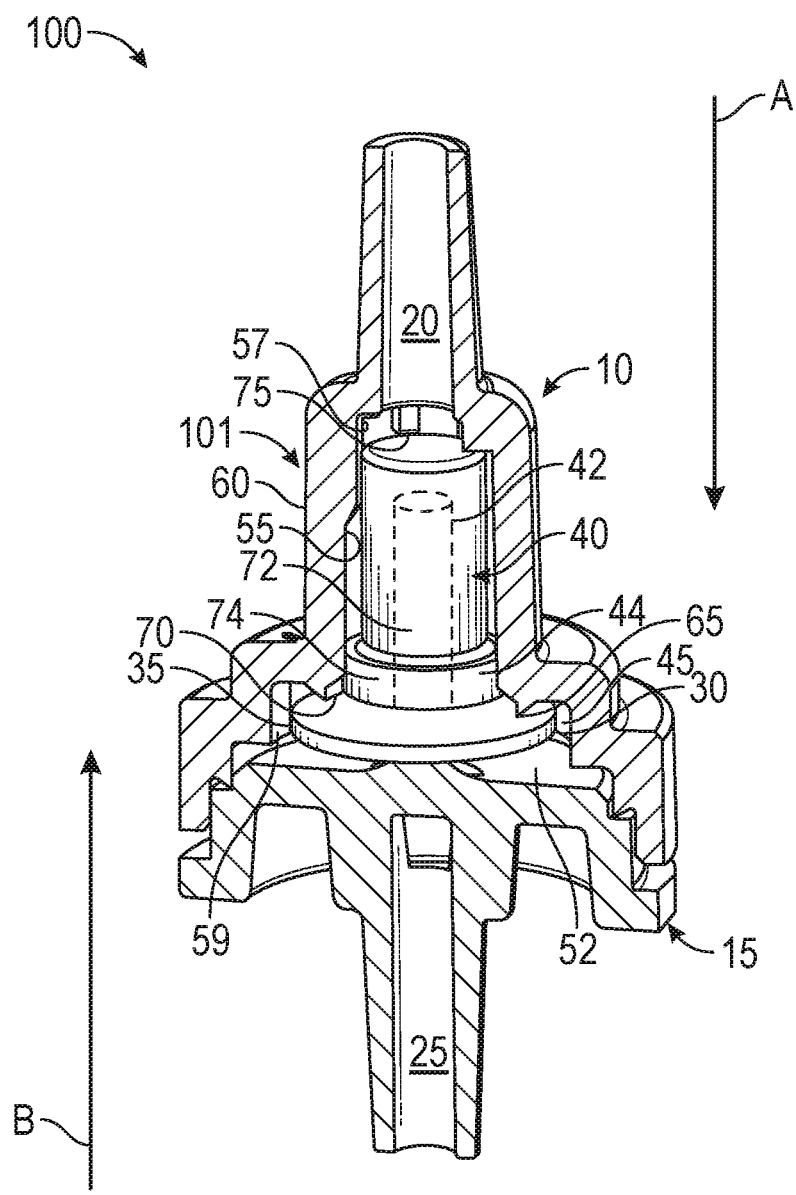
FIG. 2 illustrates the check valve in the closed state, wherein the check valve restricts fluid flow in the reverse directions, in accordance with some embodiments of the present disclosure.
Figure 3:
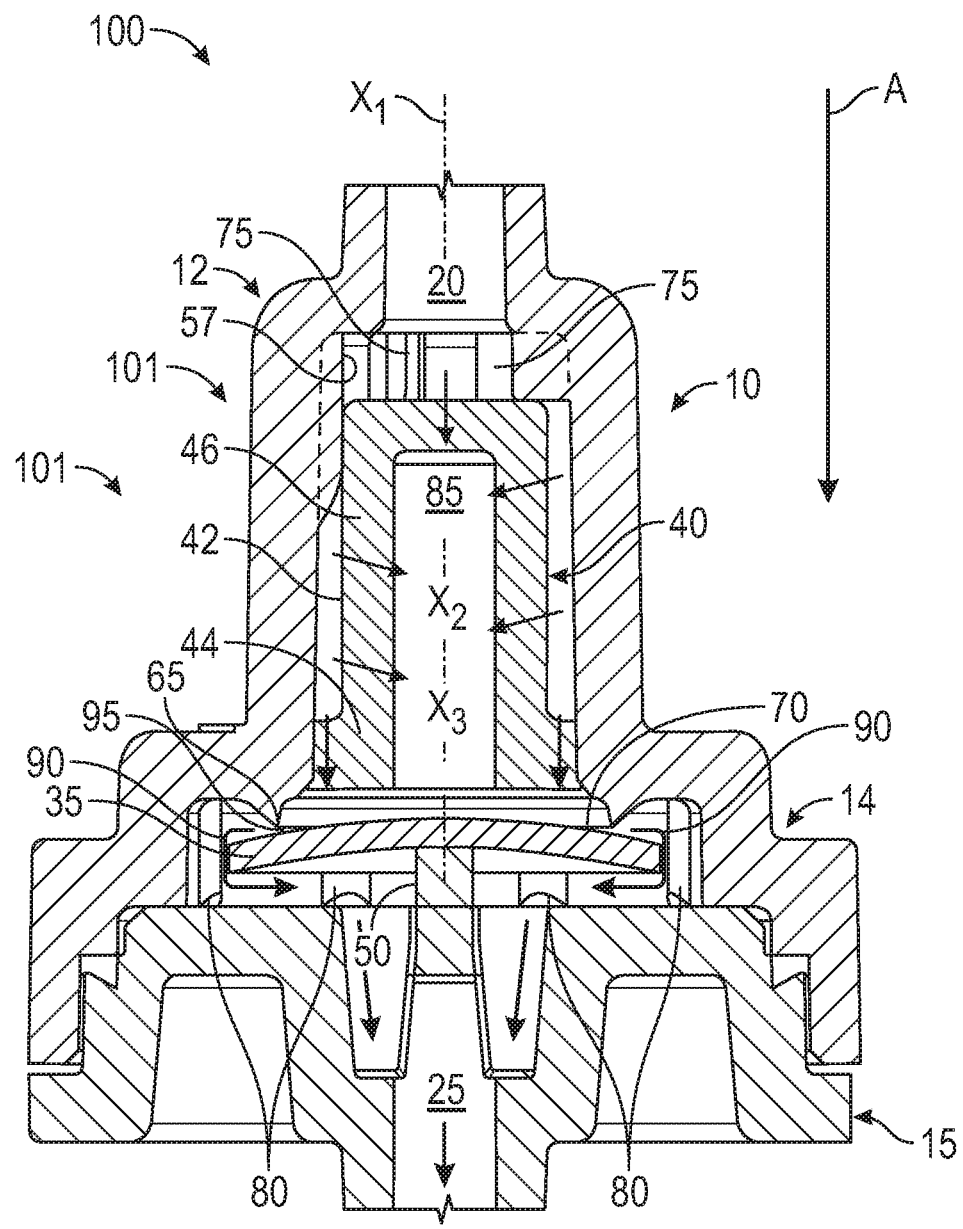
FIG. 3 illustrates the check valve in the open state when subjected to an upstream pressure, where the check valve permits fluid flow in the forward direction, in accordance with some embodiments of the present disclosure.

FIGS. 2 and 3 are cross-sectional views of check valve 100, in accordance with some embodiments of the present disclosure. FIG. 2 illustrates the check valve 100 in the closed state, where the check valve 100 restricts fluid flow in the reverse direction, in accordance with some embodiments of the present disclosure. As depicted, the upper housing 10 may include an internal surface 55 extending along the length of the interior of the upper housing 10 and defining the flow passage 85 (illustrated in FIG. 1). The upper housing 10 may further include an external surface 60 defining the exterior of the body 101. The internal surface 55 may include an upstream internal surface 57 and a downstream internal surface 59. The cavity 30 may be at least partially defined by the downstream internal surface 59 of the upper housing 102. In the depicted embodiments, the downstream internal surface 59 extends radially outward from the upstream internal surface 57. The downstream internal surface 59 may include a projection 65 which extends circularly about the central longitudinal axis $X_1$ of the body 101 and into the cavity 30. In some embodiments, the projection 65 defines a sealing surface 70 at a distal end thereof. The projection 65 and therefore the sealing surface 70 may be disposed like a ring above the valve member 35. In the normally-closed state of the check valve 100, the valve member 35 contacts the sealing surface 70. Because the valve member 35 contacts the sealing surface 70, flow of fluid in the reverse direction (illustrated by arrow B), from the outlet 25 to the inlet 20 is prevented.

During operation, when a downstream pressure (i.e., a pressure applied by a fluid flowing from the outlet 25 to the inlet 20, indicated by arrow B) is applied to the valve member 35, the valve member may deflect towards the sealing surface 70 to block the fluid communication between the inlet 20 and the cavity 30, thereby restricting backflow of the fluid from the outlet 25 to the inlet 20. Preventing backflow of the fluid is advantageous in that it restricts undesirable particulate matter, for example, contained in a drug dispensed from a secondary path from flowing back through the check valve, thereby preventing the patient from receiving the proper drug dosage concentration or from timely delivery of the drug.

In accordance with some embodiments, the valve member 35 may be formed of a flexible, resilient material which is fluid impervious. For example, the valve member 35 may be made of a silicon material. In other embodiments, however, the valve member 35 may be formed of any non-sticking, resilient material such as natural or synthetic rubber or plastic. The valve member may be formed of a material having a shore hardness of 70 or less.

In the depicted embodiments, the valve member 35 may have a generally circular disc shape corresponding to the generally cylindrical shape of the body 101 of the check valve. However, the various embodiments of the present disclosure are not limited to the aforementioned configuration. In some embodiments, the valve member 35 may have a non-circular shape, such as square, rectangular, polygonal, or any other shape capable of spanning an area sufficient to cover and overlap the sealing surface 70.

In some embodiments, the valve member 35 is not limited to any particular shape or size. In the depicted embodiments, however, the size of the valve member 35 may be limited based on desired deflection/bending characteristics of the valve member when subjected to either of the upstream or downstream forces. For example, the valve member 35 may be sized and shaped so as to flex or bend under fluid pressure to permit forward flow (from the inlet 20 to the outlet 25) of the fluid into the cavity 30 via the flow passage 85, and to limit fluid flow in the reverse direction. In some embodiments, the valve member 35 may be a curved pliable disk mounted on the support portion 50 of the lower housing 15.

As depicted, the valve member 35 may be mounted centrally within the cavity 30. For this purpose, the downstream internal surface 59 may include a plurality of ribs 80 formed thereon for aligning the valve member 35 centrally within the cavity 30. As depicted, the plurality of ribs 80 may be disposed in the cavity 30 in a manner protruding radially inward from the downstream internal surface 59. The aforementioned configuration is advantageous in that the plurality of ribs 80 act as guide members for accurate centering of valve member 35 during assembly. Thus, the ribs 80 prevent the valve member 35 from being assembled in a crooked or otherwise misaligned and undesirable manner. This will insure there is maximum surface area for filtration and cannot become restrictive if the filter was to be in contact with the inner wall.

During assembly, the valve member 35 may be mounted on the support portion 50, and the upper housing 10 may then be lowered onto the lower housing 15. The valve member 35 may be disposed to contact the sealing surface 70, with peripheral edges of the valve member 35 overlapping the sealing surface 70. As assembled, the valve member 35 may have a slight upwards bend at the peripheral edges which creates the normally-closed state of the check valve 100. The filter member 40 may be assembled in the upper housing by being pressed into and aligned in the cavity defining the flow passage 85. In some embodiments, the head portion 44 of the filter member 40 is aligned with, and press-fit into a lower portion of the cavity defined in the flow passage 85. As depicted in FIG. 1, the head portion 44 may be formed with a diameter D2 slightly larger than that of the internal surface 55 which defines flow passage 85 in which the filter member 40 is positioned. Thus, during assembly the head portion 44 may be press-fit into the internal surface 55 to form a tight interference fit with the internal surface 55. In some embodiments, a diameter D1 of the stem portion 42 of the valve member 40 may be smaller the diameter D2 of the head portion. Accordingly, when the valve member 40 is assembled in the flow passage 85, a gap 56 may be formed between the stem portion 42 and the internal surface 55. Fluid entering the check valve 100 may thus flow into the flow passage 85, through the filter member 40 where it is filtered to trap the undesirable particulate matter, and into the cavity 30, as shall be described below.

In accordance with some embodiments, the upper housing 10 may include at least one axially extending stop 75 that protrudes radially inward from the upstream internal surface 57. The at least one stop 75 may be configured as a protruding surface which is disposed directly above or upstream of the stem portion 42 of the filter member 40. The stop 75 may protrude radially inward from the upstream internal surface 57 at a distance greater than the size of the gap 56 between the internal surface 55 and an outer surface of the sidewall 68 of the stem portion 42. By protruding radially inward at a distance larger than the greater than the size of the gap 56, the stop 75 functions to prevent the filter member 40 from being displaced upwards into the inlet 20 when excessive back pressures are experienced in the check valve 100. For example, an excessive back pressure exerted on the valve member 35 may cause the valve member to deflect or bend to such an extent that it abuts the head portion 44, and exerts an upward force on the valve member 40. Due to the presence of the stop 75, the filter member 40 is prevented from being displaced upwards and into the inlet 20 as a result of the force exerted by the deflected valve member 40. As such, the filter member 40 advantageously may act as a support or safeguard to protect the valve member 35 from excessively bowing out when excessive reverse flow pressure is experienced. Further, the stops 75 also prevent the filter from "bottoming out" which would choke off flow to the cylindrical walls of the filter member 40.

FIG. 3 illustrates the check valve 100 in the open state when subjected to an upstream pressure, where the check valve 100 permits fluid flow in the forward direction, in accordance with some embodiments of the present disclosure. As depicted, during operation, fluid may enter the check valve 100 via the inlet 20, flow into the flow passage 85, through a top wall 46 of the filter member 40, and into the cavity 30. As previously discussed, since the diameter D1 of the stem portion 42 of the valve member 40 may be smaller the diameter D2 of the head portion, a gap 56 may be formed between the stem portion 42 and the internal surface 55. Fluid entering the check valve 100 may thus flow into the flow passage 85, through the top wall 46 and sidewalls of the filter member 40 where it is filtered to trap the undesirable particulate matter, and into the cavity 30. Any grit or other undesirable particulate matter larger in size than the pores of the filter member 40 may be trapped in the filter member 40, and prevented from passing downstream to the valve member 35.

The upstream pressure (i.e., pressure applied by fluid flowing from the inlet 20 to the outlet 25, indicated by arrow A) applied to the valve member 35 causes the valve member 35 to bow or bend downwards at the outer edges thereof and deflect away from the sealing surface 70. Thus, the check valve is shifted from the closed state (illustrated in FIG. 2), to an open state (illustrated in FIG. 3) where the inlet 20, the cavity 30, and the outlet 25 are fluidly communicated. In the open state, a gap 95 may be created between the sealing surface 70 and a top surface of the valve member 35 to allow the filtered fluid to flow therethrough. The filtered fluid 90 may then flow through the gap 95, into the cavity 30, and exit the check valve 100 via the outlet 25 in the lower housing 15 as indicated by the arrows.

The aforementioned configuration is advantageous in that the elongated shape of the stem portion 42 of valve member 40 provides a maximized surface area for filtration of the fluids travelling within the flow passage 85. Further, the configuration in which the filter member 40 is positioned upstream of the valve member is advantageous in that it prevents passage of undesirable particulate matter to the valve member 35 which could otherwise cause damage or wear to the valve member. The aforementioned configuration also prevents the undesirable particulate matter from potentially becoming lodged between the valve member 40 and the sealing surface 70, thereby preventing the valve member 35 from fully closing and sealing against reverse flow (backflow).

In contrast, in a conventional check valve configuration which does not include an integrated filter member, during low flow conditions, pressure exerted on the check valve as a result of the fluid flow may not be sufficient to fully open the check valve (e.g., to deflect the valve member 35) such that grit (or other undesirable particulate matter) may pass through the gap 95. In such conditions, the grit may get lodged in the gap 95 and the valve may not completely close. This undesirably causes the check valve to "weep," and allow fluid to flow through the valve in the reverse direction, thereby making the check valve ineffective.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, or operations in the processes or methods disclosed are illustrations of exemplary approaches. Based upon implementation preferences or scenarios, it is understood that the specific order or hierarchy of steps, operations or processes may be rearranged. Some of the steps, operations or processes may be performed simultaneously. In some implementation preferences or scenarios, certain operations may or may not be performed. Some or all of the steps, operations, or processes may be performed automatically, without the intervention of a user. The accompanying method claims present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A check valve, comprising:
    a lower housing defining an outlet of the check valve:
    an upper housing defining an inlet of the check valve, the upper housing comprising a projection having a distal end that extends toward the lower housing;
    a cavity interposed between and defined by the upper and lower housings for fluidly connecting the inlet and the outlet, wherein the distal end of the projection extends into the cavity to form a sealing surface;
    a flexible valve member mounted in the cavity to selectively permit fluid flow in a first direction, and to engage against the sealing surface to prevent fluid backflow in a second direction opposite to the first direction; and
    a filter member mounted in the upper housing upstream of the flexible valve member, the filter member having an elongated portion configured to maximize surface area thereof exposed to the fluid flow and restrict passage of undesirable matter in fluid flowing through the check valve.

2. The check valve of claim 1, wherein:
    the upper housing comprises a cylindrical body having an internal surface; and
    the filter member comprises a T-shaped filter including a cylindrical elongated stem portion and a head portion, the cylindrical elongated stem portion being spaced apart from the internal surface.

3. The check valve of claim 2, wherein the stem portion is mounted in the upper housing with an interference fit.

4. The check valve of claim 2, wherein the stem portion comprises a first diameter and the head portion comprises a second diameter, the second diameter being larger than the first diameter.

5. The check valve of claim 1, wherein the filter member comprises a porous material selected from the group consisting of plastic materials, cork materials, woven and nonwoven materials.

6. The check valve of claim 1, wherein:
    the lower housing comprises a support portion disposed in the cavity at a central portion thereof, a central axis of the support portion being aligned with a central longitudinal axis of the check valve; and
    the valve member is configured to be mounted and supported on the support portion.

7. The check valve of claim 1, wherein:
    the upper housing comprises an internal surface and an external surface, the internal surface including an upstream internal surface and a downstream internal surface; and
    the projection extending from the downstream internal surface of the upper housing into the cavity, the projection being circularly disposed about a central axis of the filter member.

8. The check valve of claim 7, wherein:
    when an upstream pressure is applied to the valve member, the valve member is configured to deflect away from the sealing surface to fluidly communicate the inlet and the cavity; and
    when a downstream pressure is applied to the valve member, the valve member is configured to deflect towards the sealing surface to block the fluid communication between the inlet and the cavity, and restrict backflow of the fluid from the outlet to the inlet.

9. The check valve of claim 1, wherein:
    the upper housing comprises an internal surface and an external surface, the internal surface including an upstream internal surface and a downstream internal surface; and
    the upstream internal surface comprises at least one stop protruding radially inward from the upstream internal surface to restrict axial displacement of the filter member by the valve member in the upstream direction.

10. The check valve of claim 1, wherein:
the upper housing comprises an internal surface and an external surface, the internal surface including an upstream internal surface and a downstream internal surface; and
the downstream internal surface includes a plurality of ribs formed thereon, the plurality of ribs disposed in the cavity and protruding radially inward from the downstream internal surface to center the valve member within the cavity.

11. The check valve of claim 1, wherein the filter member comprises a hollow central channel extending longitudinally through an axial center thereof.

12. The check valve of claim 11, wherein the inlet, the hollow central channel, and the outlet are aligned along a central longitudinal axis of the check valve.

13. The check valve of claim 12, wherein the inlet, the hollow central channel, and the outlet are fluidly communicated to define a flow channel through which the fluid flows through the check valve.

14. A check valve, comprising:
an upper housing comprising an internal surface forming an inlet of the check valve;
a lower housing axially coupled to the upper housing and comprising an outlet of the check valve;
a cavity cooperatively formed by the upper and lower housings for fluidly connecting the inlet and the outlet;
a flow passage extending between the inlet and outlet and fluidly communicated with the cavity;
a flexible valve member mounted in the cavity to selectively permit fluid flow in a first direction, and prevent fluid backflow in a second direction opposite to the first direction; and
an elongate filter member comprising a cylindrical elongated stem portion and a head portion, the elongate filter member mounted in the flow passage upstream of the flexible valve member with the cylindrical elongated stem portion being spaced apart from the internal surface to maximize surface area thereof exposed to the fluid flow, and restrict passage of undesirable matter in fluid flowing towards the flexible valve member.

15. The check valve of claim 14, wherein the filter member is mounted in the upper housing by press-fitting into the flow passage in the upper housing.

16. The check valve of claim 14, wherein the filter member comprises a hollow central channel extending longitudinally through at least a portion of the head portion and the stem portion.

17. The check valve of claim 16, wherein the inlet, the hollow central channel, and the outlet are co-axially aligned with each other.

18. The check valve of claim 14, wherein:
an internal surface of the upper housing in the cavity includes an axially extending projection disposed circularly about the flow passage in the cavity; and a sealing surface is defined at a distal end of the circular projection, wherein the valve member is configured to contact the sealing surface to limit fluid flow across the sealing surface.

* * * * *